(12) United States Patent
Perren

(10) Patent No.: US 10,722,368 B2
(45) Date of Patent: Jul. 28, 2020

(54) TISSUE EXPANSION BOOSTER

(71) Applicant: Nicolas Perren, Dessau (DE)

(72) Inventor: Nicolas Perren, Dessau (DE)

( * ) Notice: Subject to any disclaimer, the term of this patent is extended or adjusted under 35 U.S.C. 154(b) by 105 days.

(21) Appl. No.: 15/579,145

(22) PCT Filed: May 23, 2016

(86) PCT No.: PCT/IB2016/000710
§ 371 (c)(1),
(2) Date: Dec. 1, 2017

(87) PCT Pub. No.: WO2016/193801
PCT Pub. Date: Dec. 8, 2016

(65) Prior Publication Data
US 2018/0168810 A1 Jun. 21, 2018

(30) Foreign Application Priority Data
Jun. 3, 2015 (DE) .................. 20 2015 004 095

(51) Int. Cl.
*A61F 2/28* (2006.01)
*A61B 17/68* (2006.01)
*A61F 2/30* (2006.01)
*B33Y 80/00* (2015.01)

(52) U.S. Cl.
CPC .......... *A61F 2/28* (2013.01); *A61B 2017/681* (2013.01); *A61F 2002/286* (2013.01); *A61F 2002/2817* (2013.01); *A61F 2002/30224* (2013.01); *A61F 2002/30565* (2013.01); *A61F 2310/00395* (2013.01); *A61F 2310/00592* (2013.01); *A61F 2310/00976* (2013.01); *B33Y 80/00* (2014.12)

(58) Field of Classification Search
CPC ....... A61F 2002/30706; A61B 17/7216; A61B 2017/681
See application file for complete search history.

(56) References Cited

U.S. PATENT DOCUMENTS

2005/0113924 A1* 5/2005 Buttermann ....... A61B 17/1671
623/17.13
2008/0167720 A1* 7/2008 Melkent .................... A61F 2/44
623/17.16

FOREIGN PATENT DOCUMENTS

DE 102008064628 A1 9/2009

OTHER PUBLICATIONS

German Search Report in connection with Application No. DE 202015004095 dated Dec. 15, 2015.
(Continued)

*Primary Examiner* — Megan Y Wolf
(74) *Attorney, Agent, or Firm* — Steven M. Shape; Dennemeyer & Associates, LLC

(57) ABSTRACT

An implant (1) for modifying the tissue deformation during bone healing between two bone fragments (5; 6), with a first end piece (2) that can be fastened to a first bone fragment (5) with a longitudinal axis L1, and a second end piece (3) that can be fastened to a second bone fragment (6) with a longitudinal axis L2, wherein the first and second end pieces (2; 3) are loosely meshed with one another by means of n≥1 parallel-connected tissue activators (4a; 4b) in each case to allow relative movement and the tissue activators (4a; 4b) are arranged to be perpendicular to the longitudinal axes L1 and L2 and preferably orthogonal thereto.

16 Claims, 4 Drawing Sheets

(56) References Cited

OTHER PUBLICATIONS

Halvachizadeh S., Pape HC., "Perren's Strain Theory and Fracture Healing," Essential Biomechanics for Orthopedic Trauma, p. 17-25, published Mar. 1, 2020.
Lee Van Rensburg, Basic Science Course Lecture, "Fracture Healing," published 2014.
Edmund Y.S. Chao and Nozomu Inoue, "Biophysical Stimulation of Bone Fracture Repair Regeneration and Remodelling" European Cells and Materials vol. 6, pp. 72-85, 2003.

* cited by examiner

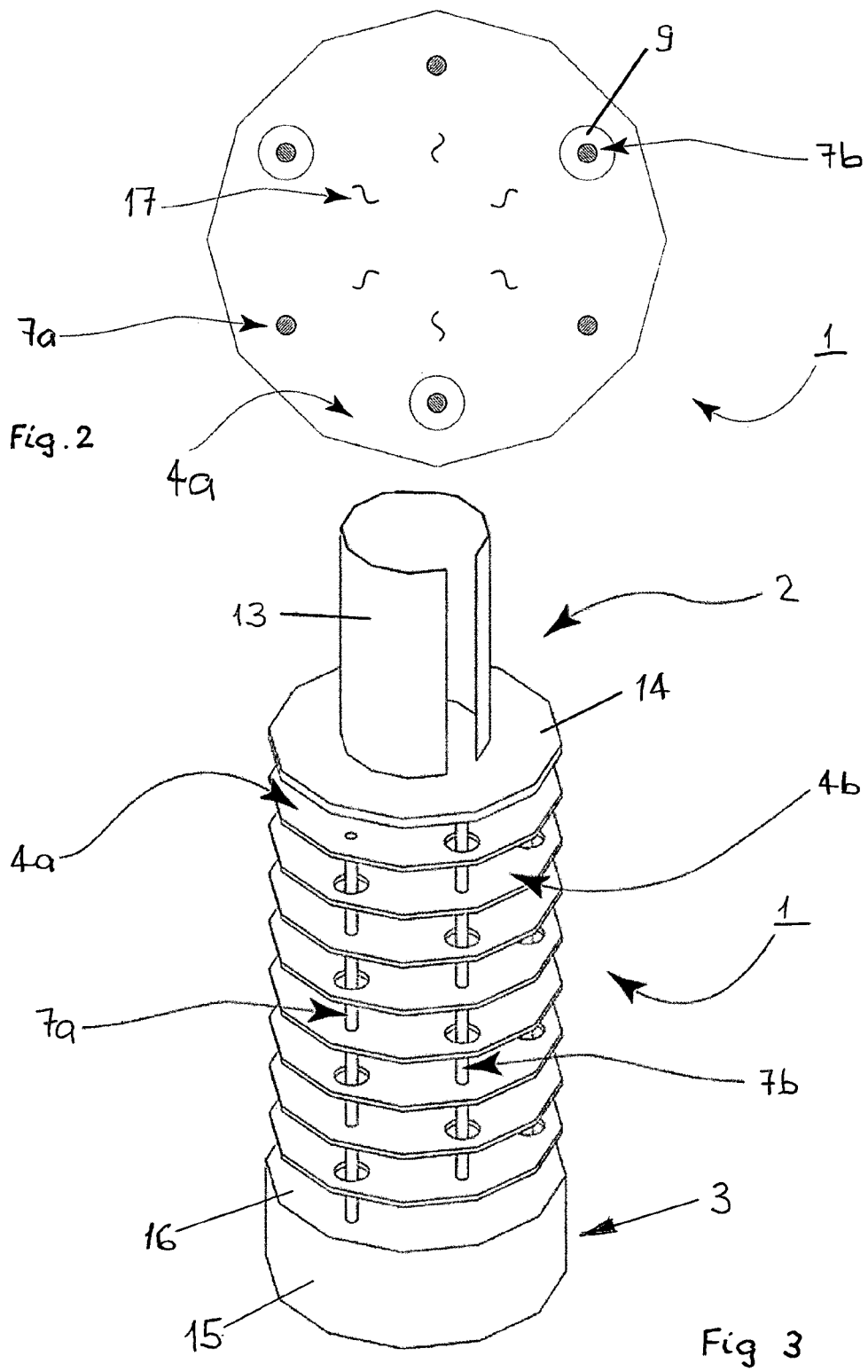

TISSUE EXPANSION BOOSTER

CROSS-REFERENCE TO RELATED APPLICATIONS

This is a 35 U.S.C. 371 National Stage Patent Application of International Application No. PCT/IB2016/000710, filed May 23, 2016, which claims priority to German application 202015004095, filed Sep. 6, 2016, each of which is hereby incorporated by reference in its entirety.

The invention relates to an implant, especially to a tissue expansion amplifier according to the preamble of claim 1.

The bone supports the elements of the locomotor apparatus and in this way, enables its functioning. When it is broken due to overloading, the bone loses its mechanical functioning. The restoration of the functioning of the broken bone, or fracture healing, requires solid bridging of the fracture in an anatomically correct position. A successful fracture healing must be induced, enabled and maintained. The mechanical conditions play a decisive role in this process. This is true not only for fracture healing, but also for tissue healing in general, as well as for the creation of tissues inside or outside of the human body (e.g., tissue engineering).

Definitions

Expansion (symbol ε): In the following, expansion will be used to designate the relative change in length (lengthening or shortening) in various directions of a body under a load, for example by a force. If the dimension of the body is increased, this is called positive expansion, and the opposite, negative expansion or compression.

A critical element of mechanics with regard to bone healing is tissue deformation (elongation ε in the sense of lengthening and shortening, in various directions). On one hand, healing is stimulating if tissue expansion exceeds a minimum quantity. If expansion is too little, the healing process is not triggered. On the other hand, bridging of the fracture is only possible if the existing expansion of the tissue element is not greater than the breaking elongation of the tissue undergoing repair. A range of expansion exists between these two conditions, induction and tolerance, and this is prerequisite for expeditious and reliable healing. If the interfragmentary expansion is outside of the range mentioned, healing is disturbed. Delayed healing or pseudarthrosis develops. Treatment of such healing disorders requires correction of the tissue expansion. By increasing or decreasing, the expansion can be modified to the range mentioned, and thus healing can be made possible.

A bone anchoring or connecting device is known from document WO 2012/045307. This known device provides a construction in which the two end plates are rigidly connected to one another. Thus, it involves a supporting connecting element that serves for stabilising the bridged bone fragments.

This known implant comprises a rigid implant carrier connecting the two end plates and structural supports arranged on the periphery of the implant carrier, which are largely decoupled from the implant carrier, but are connected to the implant carrier in the area of the interfaces with the bone in at least one place. The structural supports have a structure in the form of regularly or irregularly arranged fins, grids, shapes, drilled holes or cavities. When the patient places a load on the implant, the structural supports undergo relative movements, wherein the rigidity of the implant support and the arrangement of the structural supports are selected such that the stretch stimulus imposed on the tissue by the structural support leads to accelerated formation of bone cells.

One disadvantage in this known device is that due to the rigidity of the implant carrier, the movement of the bone is reduced, compromising the desired increase in expansion.

This known device thus has specific objectives, namely
producing a rigid connection of the end plates, which provides for force transfer; and
increasing the stretch stimulus due to the movement between the structural supports connected to the end plates.

When a force or torque acts on the implant, the implant support is deformed, e.g., undergoes a change in length ΔL. The structural supports are firmly connected with one or the other end plate and themselves are formed to be rigid, so that the structural carriers do not undergo any appreciable deformation during the deformation of the implant carrier, i.e., the fins or grids are displaced by the same ΔL (absolute change in length ΔL) relative to one another. By selecting the distance between the indentations on two fins opposite one another, the local expansion of the tissue that results from the relative displacement of the fins, in combination with the rigidity of the implant carrier, can be adjusted to practically any arbitrary extent.

A further disadvantage of this known implant is that the force transfer rod is mounted centrally in the construction, and thus at the point where the bone marrow is located in a long bone. Thus, bone marrow formation is not possible with this known implant.

The invention aims to remedy this. The invention has the object of creating a bone implant which due to its design produces contiguous regions of optimal expansion, e.g., in the fracture gap. In this way, for example, a solid bone bridge is induced from one bone fragment to the other and thus avoids expansion that is too small or too large, which interferes with healing.

The reduction of the effective distance between the bone fragments is accomplished with the aid of elements that divide the distance to be bridged into smaller sections by parallel connection, wherein a larger expansion is made possible with these smaller sections.

If no implant according to the invention is inserted between the surfaces of the adjacent bone fragments, the movement of the bone fragment relative to one another results in a small expansion because of the large distance between the bone fragments. If the expansion mentioned is too small, the healing process is not stimulated. By inserting an implant according to the invention between the bone fragments, the same relative movement is transferred to the bone material arranged between the tissue activators. Since the tissue activators divide the total space between the bone fragments into several longitudinal sections, the tissue arranged between two tissue activators or between an end piece and a terminal tissue activator undergoes greater expansion because of the smaller height of this tissue space relative to the fracture gap, inducing and sustaining the healing process.

The invention achieves the object posed with an implant having the features of claim 1.

The advantages achieved by the invention compared with the prior art are essentially that:
The ends connected with the bone fragments can move freely relative to one another, since they are not connected by force-fit, and thus the expansion of decisive significance for healing is retained. The activators, connected with the respective ends, produce an optimised expansion over the entire range;
In contrast to the prior art, the implant according to the invention can permit the formation of bone marrow.

The construction allows for great variability in the design of the activators including the design of free spaces at essential points, continuous or offset;

In contrast to the prior art, the bone material plugs arranged between two activators and subjected to expansion extend over the entire cross-sectional surface of the bone, whereas in the known implant only the tissue in the marginal areas of the implant is subjected to an optimal stretch stimulus;

The activators, in contrast to the known implant, are connected directly to the end pieces and thus the area of optimised expansion extends from end to end; and The activators, in contrast to to the known implant, are not continuous, for example porous, and thus the expansion-optimised area extends over several levels.

The invention can be used wherever tissue differentiation is stimulated or enabled by correction or creation of the optimal expansion. Among other things, for example, the generation of soft tissue or bone for therapeutic or aesthetic application is part of the invention. In bone elongation using the Illizarov method, elongation is currently produced in millimetre steps, since the result of a larger step would cause too little expansion to generate reliable bone formation. The disadvantage of the method mentioned is that the patient must tolerate wearing the cumbersome external braces. By using the implant according to the invention, the optimal expansion for bone formation is achieved even in centimetre expansion steps. The wearing time of the fixators, which are bothersome for the patients, can be substantially shortened or avoided. In the case of surgical operations that require transplantation of autologous (endogenous) bone, the necessary bone removal, e.g., from the pelvis, causes rather long-lasting, bothersome pain. The implant according to the invention, when implanted in a patient, can induce bone formation without the painful consequences of bone removal as mentioned.

The advantages achieved with the invention essentially consist of the fact that due to the implant according to the invention, optimal extension can be achieved by changing the distance between elements exposed to the movement of bone fragments.

The implant according to the invention functions in the case of all movements that deform the tissue, such as axial movements (compression and expansion), flexion, torsion, parallel shifts, and other movements, as well as with combinations of movement components.

The implant according to the invention can be used to promote healing at defined locations. However, it can also serve to produce certain tissues in the body, which are used for "tissue engineering" in general.

The implant according to the invention can also be used for bone elongation. It is possible to achieve such elongations up to as much as several centimetres in a single step. This is the essential advantage versus the known Illizarov method which allows only millimetre elongation steps. Thus, bone elongation can be achieved in a single step or a few steps with the implant according to the invention. Shortly after the operation, the patient is fully functional again, and wearing movement-hindering external fixator constructions therefore becomes superfluous.

Additional advantageous embodiments of the invention can be commented upon as follows:

The planes of the tissue activators can be inclined in various directions.

In a specific embodiment, one or more spring-like elements are arranged between at least two tissue activators.

In a further embodiment, the implant has a wrapping of essentially cylindrical or prismatic shape, wherein a jacket that may surround the wrapping accounts for a maximum of 40%, preferably at most 20% of the total surface area of the wrapping. The implant known from the prior art has an extended cylindrical jacket surface that is penetrated only by small-slots or perforations, so that the ingrowth of tissue into the implant is strongly impeded.

In a further embodiment, the tissue activators are designed and mutually arranged in such a manner that they allow the ingrowth of tissue. The structure of the tissue activators is intended to enable solid ingrowth of blood vessels and restorative tissues between and within the tissue activators.

In another embodiment, the tissue activators are plate-shaped, bar-like, mesh-like or rod-shaped. The tissue activators may be implemented as complete plates, but also as parts of plates, e.g., plate segments or other regular or irregular shapes; the plate parts can be parts of the plate located adjacent to one another, arranged in staggered form or networked. The tissue activators can also be designed such that these have a central recess.

In another embodiment, the tissue activators are porous.

In yet another embodiment, the opposing surfaces of the tissue activators are plane-parallel, curved or oblique. The surfaces may be arched or curved in various ways, so that the distance mentioned changes from place to place and, for example, generates sites of optimal expansion.

In an additional embodiment, the tissue activators consist of tissue-compatible plastics, metals, metal alloys or ceramic.

In another embodiment, the tissue activators consist of bioresorbable materials. This offers the advantage that the implant dissolves over time and disappears.

In another embodiment, the surfaces of the tissue activators and/or the interstices between the tissue activators contain substances that promote healing and bone building, preferably bone morphogenic protein or bone meal.

In another embodiment, the surfaces of the tissue activators and/or the interstices between the tissue activators are provided with stem cells. In this manner it is possible to achieve the advantage that healing and bone building are thereby promoted.

In yet another embodiment, the interstices between the tissue activators are filled with an open-pore structure.

In a further embodiment, the first and second end piece are designed such that they allow a force-fit mechanical coupling to the two bone fragments, preferably (i) mechanically by means of press fitting, screwing, nailing, plating or sewing, or (ii) chemically by means of adhesive bonding.

In a further embodiment, the connection of the tissue activators with the end pieces is realised with individual or multi-part load-bearing elements.

In another embodiment, the load-bearing elements are alternately firmly fixed on a tissue activator or cross over this without contact. The alternating connection mentioned can also be formed by bridging constructions which, for example, are attached to the peripheries of the activators.

In another embodiment, the first end piece is connected by means of one or more first load-bearing elements with n≥1 first tissue activators and the second end piece is connected by means of one or more second load-bearing elements with n≥1 second tissue activators.

In a further embodiment, the first end piece is rigidly connected by means of one or more first load-bearing elements with the n≥1 first tissue activators.

In a further embodiment, the second end piece is rigidly connected by means of one or more second load-bearing elements with the n≥1 second tissue activators.

In yet another embodiment, the first end piece is connected loosely, preferably movably, by means of one or more first load-bearing elements, with at least one of the n≥1 first tissue activators.

In a further embodiment, the second end piece is connected loosely, preferably movably, by means of one or more second load-bearing elements, with at least one of the n≥1 second tissue activators.

Preferably the first implant according to the invention is suitable for the treatment of bone fractures and bone defects and for creating bone tissue.

One embodiment of a method for producing the implant according to the invention comprises essentially the following steps:

A) Determining the length of the fracture gap to be bridged;
B) Determining the number of tissue activators of the implant based on the desired expansion of the tissue material interposed between the tissue activator; and
C) Preparing an implant with the number of tissue activators determined under step B).

The complex structure of the strain modifier can be produced mechanically, e.g., by 3D printing, e.g., of bioresorbable polylactide (PLA) or also by CNC milling, laser cutting, welding, water jet cutting or other methods of applying or removing material. The implant according to the invention can also be custom-made using the above-mentioned methods. This production can take place during the surgical procedure.

The invention and further embodiments of the invention will be explained in detail below based on the partially schematic illustrations of several examples.

The following is shown in the drawings:

FIG. 2 is a section along line A-A in FIG. 1;

FIG. 3 is a perspective view of the implant according to FIG. 1;

Figure 1:
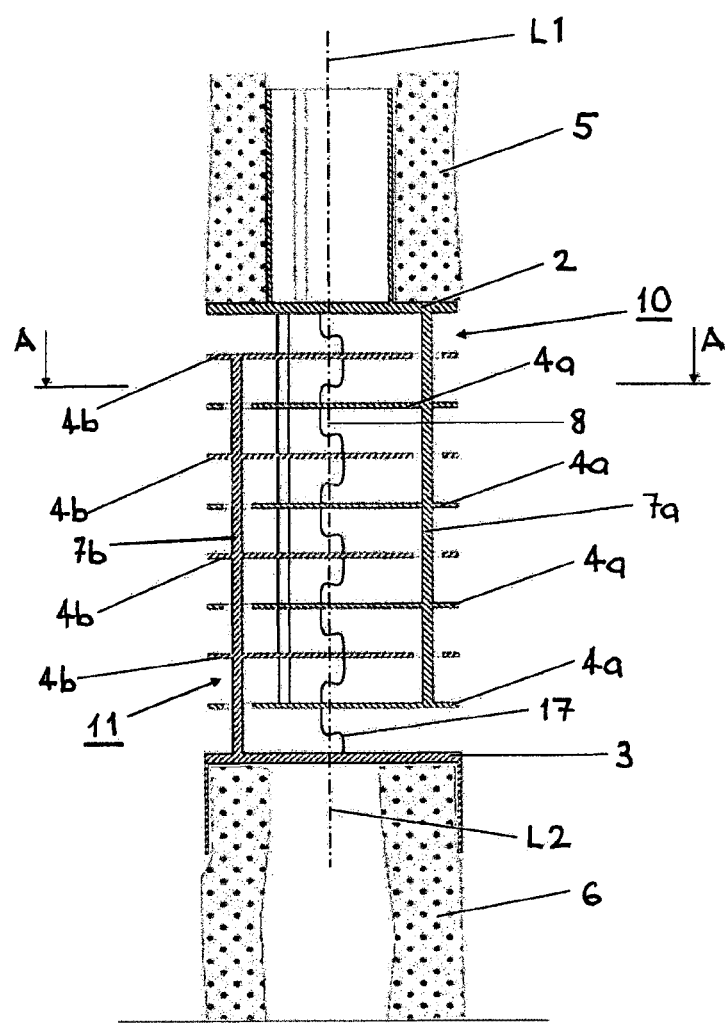
FIG. 1 is a longitudinal section through an embodiment of the implant according to the invention.

The embodiment of the implant 1 according to the invention shown in FIGS. 1-3 comprises a first end piece 2, a second end piece 3 and several tissue activators 4a; 4b, which are alternatingly connected to one each of the end pieces 2; 3, wherein a first group of tissue activators 4a is arranged in a parallel connection and with the first end piece 2 forms a first component 10, which can be fastened to a first bone fragment 5, and a second group of tissue activators 4b is likewise arranged in a parallel connection and with a second end piece 3, forming a second component 11, which can be fastened to a second bone fragment 6. By alternately connecting the tissue activators 4a; 4b with the end pieces 2; 3, a parallel connection is achieved, which reduces the active distance over which the mutual movement of the adjacent bone fragments 5; 6 takes effect so that the expansion between the tissue activators 4a; 4b is increased. In particular, the implant 1 comprises a first end piece 2 with a longitudinal axis L1, which can be fastened to a first bone fragment 5, a second end piece 3 with a longitudinal axis L2, which can be fastened to a second bone fragment 6, and two groups of, as a non-limiting example, in each case four parallel tissue activators 4a; 4b, wherein each group of tissue activators 4a; 4b is connected with one each of the first and second end pieces 2; 3. The tissue activators 4a; 4b of each of the two groups are arranged at intervals from one another and alternately mesh with one another along a central axis 8 of the implant 8, in such a manner that the first and second end piece 2; 3 loosely mesh with one another, so that a relative movement of the first and second end pieces 2; 3 is guaranteed. The tissue activators 4a; 4b are arranged perpendicularly, and especially in the embodiment shown here, as a non-limiting example, orthogonal to the longitudinal axes L1 and L2 of the first and second end pieces 2; 3. The longitudinal axis L1 of the first end piece 2 and the longitudinal axis L2 of the second end piece 3 in the embodiment of the implant 1 according to the invention shown here are coaxially arranged and define a central axis 8 of the implant 1, which is likewise arranged coaxially to the longitudinal axes L1, L2.

The tissue activators 4a; 4b transfer the motion of the end pieces 2; 3 to the spaces between the tissue activators 4a; 4b mentioned and thus increase the expansion of the deformation produced by the movement of the end pieces 2; 3, which now, instead of the total distance between the end pieces 2; 3, takes place on the smaller distance between the tissue activators 4a; 4b. In this way the expansion of the material present between the tissue activators 4a; 4b is increased; the poorly healing bone fracture or -defect serves as an example. An increase in expansion of this type is decisive for bringing about healing of the bone defect or bone fracture.

Through serial connection of a spring element 17, reduction of the expansion between the tissue activators 4a; 4b [decreased expansion] can be attained. The spring element 17, as a non-limiting example, may be implemented as a coil spring, wound or folded element, in regular or free form.

Alternatively, only the end pieces 2; 3 may be connected with the respective packet of tissue activators 4a; 4b, but not reciprocally. The movement of the end pieces 2; 3 is then not reduced.

The first and second end piece 2; 3 are essentially formed such that they enable force-fit connection to one of the two bone fragments 5; 6 in each case, wherein the following couplings or combinations thereof are particularly suitable: (i) mechanically by means of press fitting, screwing, nailing, plating or sewing, or (ii) chemically by means of adhesive bonding.

FIG. 3 shows a perspective view of this embodiment of the implant 1 according to the invention obliquely from above. The load-bearing elements 7a; 7b are alternatingly connected with the tissue activators 4a; 4b or cross over these without connection. By way of example, the connection of the tissue activators 4a; 4b with the bone fragments 5; 6 is shown as a slotted sleeve, slotted tube or "marrow nail", which permits press fitting. However, the implant 1 can also be inserted without connecting elements between the bone fragments 5; 6.

In the embodiment shown in FIG. 1-3, the first end piece 2, as a non-limiting example, comprises a longitudinal section 13 in the form of a slotted tube, which can be clamped firmly in the medullary cavity of the first bone fragment 5, and at the end of this longitudinal section 13 orthogonal to the longitudinal axis L1 is arranged an end plate 14 for attachment to the front face of the first bone fragment 5 facing the fracture gap. The tissue activators 4a of the first group and the first end piece 2 are connected together by means of first load-bearing elements 7a and form a first rigid component 10. Here, the end plate 14 of the first end piece 2 and the adjacent tissue activator 4a tissue activator and the tissue activators 4a of this first group, arranged at equal intervals to one another along the central axis 8 of the implant 1, as a non-limiting example, are connected by means of three first load-bearing elements 7*a* (FIG. 2).

In analogy to this, the second end piece 3 comprises a longitudinal section 15 in the form of a tube, which can be pressed over the outer surface of the second bone fragment 6, and arranged at the end of this longitudinal section 15, an end plate 16 for attachment to the front face of the second bone fragment 6 facing the fracture gap. The tissue activators 4*b* of the second group and the second end piece 3 are connected together by means of two load-bearing elements 7*b* and form a second rigid component 11. Here, the end plate 16 of the first end piece 3 and the adjacent tissue activator 4*b* tissue activator and the tissue activators 4*b* of this second group, arranged at equal intervals to one another along the central axis 8 of the implant 1, as a non-limiting example, are connected by three second load-bearing elements 7*b* (FIG. 2).

The first and second load-bearing elements 7*a*; 7*b* can be implemented as rods, clamps, or from other elements that rigidly connect the tissue activators 4*a*; 4*b* alternately with the first and second end pieces 2; 3. Thus, each of the first and second load-bearing elements 7*a*; 7*b* can be formed in one or more pieces. The load-bearing elements 7*a*; 7*b* extend essentially in parallel to the central axis 8 of the implant and are alternately firmly fixed on a tissue activator 4*a*; 4*b* or cross over this without contact. Alternatively, the load-bearing members 7*a*; 7*b* at the peripheries of the tissue activators 4*a*; 4*b* can be fastened to one group in each case and pass to the outside at the peripheries of the tissue activators 4*a*; 4*b* of the respective other group.

In the embodiment of the implant 1 according to the invention shown in FIG. 1-3, the end plates 14; 16 of the first and second end pieces 2; 3 and the tissue activators 4*a*; 4*b* are formed as plates with a polygonal periphery. As is apparent in FIG. 2, three load-bearing elements 7*a*; 7*b* per alternating packet of tissue activators 4*a*; 4*b* freely cross over the tissue activators 4*a*; 4*b* of the one packet and are connected firmly to the tissue activators 4*a*; 4*b* of the other packet. The load-bearing elements 7*a*; 7*b* of each component 10; 11 are, as a non-limiting example, arranged in a peripheral area of the tissue activators 4*a*; 4*b*, in each case at the angles of an equilateral triangle, wherein the first and second load-bearing elements 7*a*; 7*b* are at equal distances from one another. In this instance, the three load-bearing elements 7*a* of the first component 10 are firmly fixed on each tissue activator 4*a* of the first group, while the three load-bearing elements 7*b* of the second component 11 are passed through appropriately positioned holes 9 in each of the tissue activators 4*a* of the first group. Analogously, the three load-bearing elements 7*b* of the second component 10 are firmly fixed to each tissue activator 4*b* of the second group, while the three load-bearing elements 7*a* of the first component 10 are passed through appropriately positioned holes 9 in each of the tissue activators 4*b* of the second group. Alternatively, the tissue activators 4*a*; 4*b* may be bar-like, mesh-like or rod-shaped. The tissue activators 4*a*; 4*b* may be implemented as complete plates, but also as parts of plates, e.g., plate segments or other regular or irregular shapes, wherein the plate parts can be parts of a plate, located adjacent to one another, arranged in staggered form or networked.

Since both components 10; 11 are rigidly constructed, i.e., the tissue activators 4*a*; 4*b* of each of the two groups are firmly fixed to the corresponding end piece 2; 3, a load, for example applied to the first bone fragment 5, will be transferred over the first end piece 2 as a compressive force onto the first component 10 with the tissue activators 4*a* of the first group, so that the distance between the end plate 14 of the first end piece 2 and the terminal tissue activator 4*b* of the second component 11 is shortened, and a negative extension or compression of the bone material located between them takes place. On the other hand, the distance is increased between the terminal tissue activator 4*b* of the second component 11 and the first tissue activator 4*a* of the first component 10, i.e., the tissue activator 4*a* of the first group, which is adjacent to the first end piece 2, so that a positive expansion of the one elongation of the bone material located in between takes place if this is fixed on the tissue activators 4*a*; 4*b*.

In various embodiments of the implant 1 according to the invention, the tissue activators 4*a*; 4*b* may be porous. In addition, the opposing surfaces of the tissue activators 4*a*; 4*b* may be of plane-parallel, curved or oblique design, wherein the surfaces may be arched or curved in various ways, so that the interval between pairs of tissue activators 4*a*; 4*b* changes from place to place and, for example, generates sites of optimal expansion. The tissue activators 4*a*; 4*b* are made of tissue-compatible plastics, metals, metal alloys or ceramic, or may also consist of bioresorbable materials.

The surfaces of the tissue activators 4*a*; 4*b* and/or the interstices between the tissue activators 4*a*; 4*b* comprise substances (not shown) that promote healing and bone building, preferably bone morphogenic protein or bone powder. In another embodiment, the surfaces of the tissue activators 4*a*; 4*b* and/or the interstices between the tissue activators 4*a*; 4*b* may be provided with stem cells to promote healing and bone formation. Alternatively, or additionally, the interstices between the tissue activators 4*a*; 4*b* may be filled with an open-pore structure.

Figure 4:
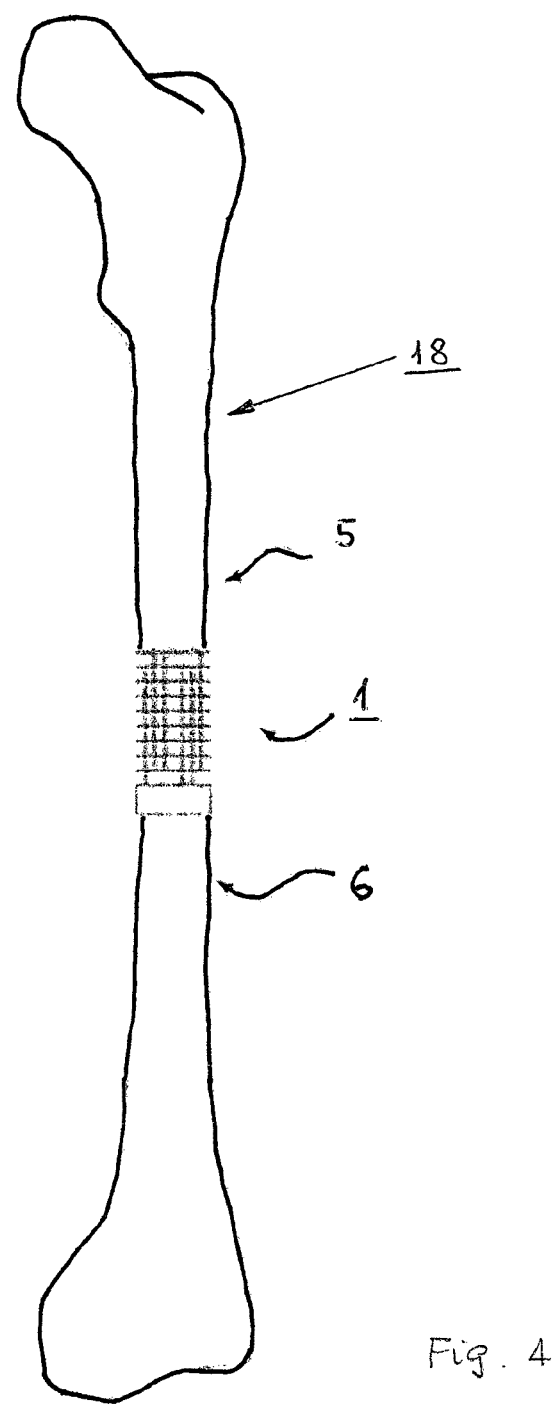
FIG. 4 is a schematic representation of the implant inserted between two bone fragments according to FIG. 1.

The implant 1 according to the invention shown in FIG. 4 in this example serves to replace a poorly healing or non-healing segment of a long bone 18, e.g., a femur, between a first and a second bone fragment 5; 6. Other applications are not bound to this example of the cortical long bone. The implant 1 according to the invention can also be used in cancellous bone and in bone defects. The tissue differentiation created by optimising the expansion not only applies to that of the bone but also to the differentiation of the soft tissue.

Figure 5:
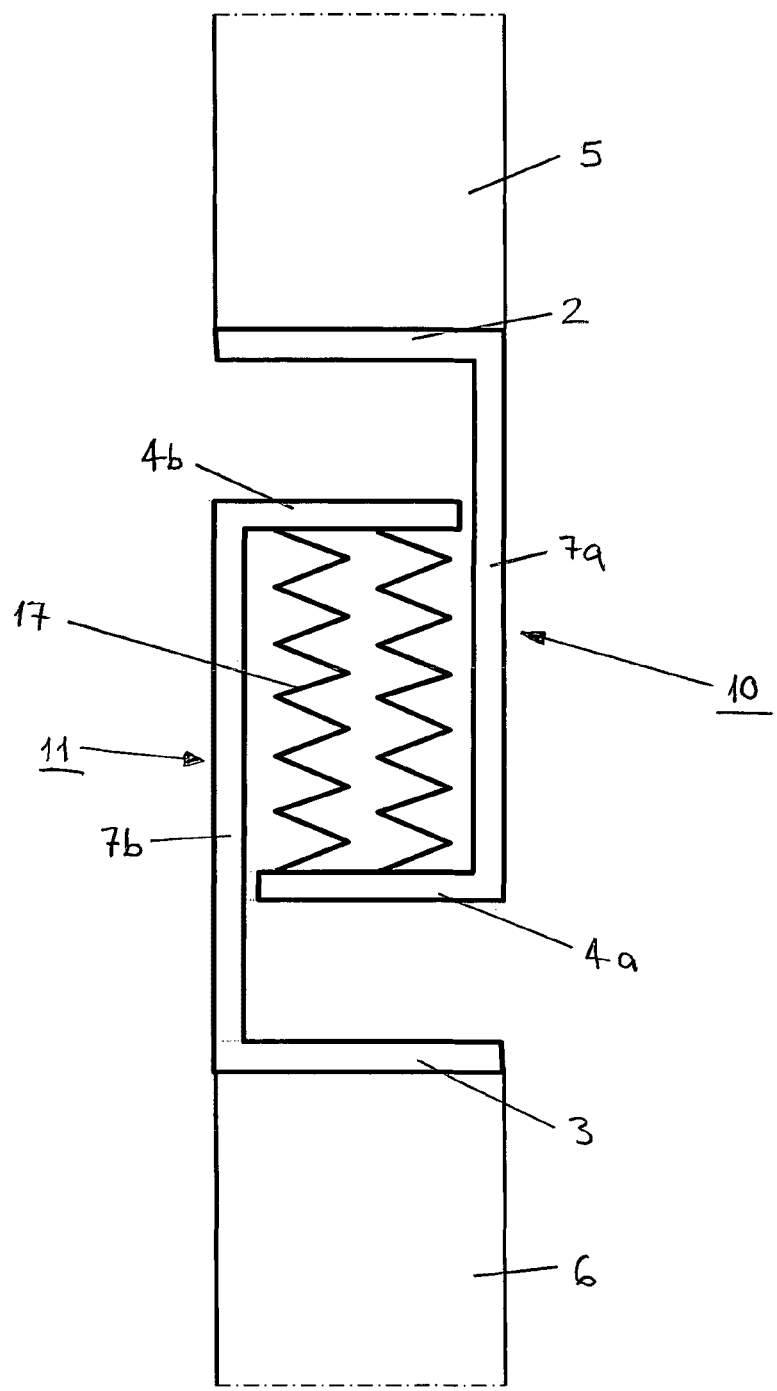
FIG. 5 is a schematic representation of a further embodiment of the implant according to the invention.

The embodiment of the implant 1 according to the invention shown in FIG. 5 differs from the embodiment shown in FIG. 1-3 only in that the implant 1, as a non-limiting example, comprises only one tissue activator 4*a*, 4*b* per group, i.e., per component 10; 11, and that spring elements 17 are inserted between the tissue activators 4*a*; 4*b*. As described above, the optimal tissue expansion falls within the range between expansion that is too small, which does not induce healing, and excessive expansion, which does not enable bridging of the fracture by callus formation. Solid healing is prevented by the latter. The implant 1 according to the invention enables an increase in the case of expansion that is too small, and as a result of the spring element 17 of the embodiment shown in FIG. 4, also enables reduction of an excessive expansion. As a non-limiting example, two spring elements 17 are inserted between the tissue activators 4*a*; 4*b*. Alternatively, other elastically deformable elements may also be used.

Through the spring elements 17, a load acting on the bone fragments is opposed by an additional but very small resistance. The spring elements 17 serve for distributing the expansion and have no supporting function. To create areas that are subjected to different expansions, it is provided that the surfaces of the activators 4*a*; 4*b* may be made curved and not plane-parallel. The tissue activators 4a; 4b can be connected to the load-bearing elements 7a; 7b rigidly or non-rigidly, i.e., movably. For example, terminal stops may be arranged on the load-bearing elements 7a; 7b, so that the tissue activators 4a; 4b remain connected to the load-bearing elements 7a; 7b.

As mentioned above, the optimal tissue deformation (expansion) falls within a range between expansion that is too small, at which healing is not induced, and excessive expansion, which does not enable bridging of the fracture by callus formation. The latter does not provide for solid healing. The implant according to the invention makes it possible to increase an expansion that is too small, but is also suitable for reducing excessive expansion based on the following modification:

Spring-like elements or spring elements 17 are introduced between the tissue activators 4a; 4b. Along these spring elements 17, which considerably increase the distance between the tissue activators 4a; 4b, the tissue is subjected to reduced deformation, since for this movement the distance over which the tissue is deformed is increased severalfold. In this way the size of the tissue deformation is reduced. The effect of this increase in the distance because of the use of spring elements 17 is several-fold larger than the effect of a shorter distance between the tissue activators 4a; 4b, which would increase the expansion. Thus, in an implant 1, areas of larger expansion (directly connected between the tissue activators 4a; 4b) and areas of lesser expansion are established along the spring elements 17.

The tissue, which undergoes optimal expansion, either between the tissue activators 4a; 4b or along the spring elements 17, enables healing, wherein it is not necessary for correct functioning that the same expansion conditions be present overall. Healing begins in the areas with optimal expansion, and the subsequent solid bridging reduces the displacement between the ends of the fragments or between the ends of the implant 1, so that healing over the entire cross-section becomes possible.

Although various embodiments of the present invention exist, as described above, these are to be understood as meaning that the various features can be used individually and also in any arbitrary combination.

Therefore, this invention is not simply limited to the particularly preferred embodiments mentioned above.

The invention claimed is:

1. An implant (1) for modifying the tissue deformation during bone healing between two bone fragments (5; 6), the implant comprising:
   (i) a first end piece (2) configured to be fastened to a first bone fragment (5) with a longitudinal axis L1;
   (ii) a second end piece (3) configured to be fastened to a second bone fragment (6) with a longitudinal axis L2;
   (iii) at least one tissue activator connected to one of the first end piece and the second end piece, wherein
   a) the first end piece and the second end piece are loosely meshed with one another by the at least one tissue activator allow relative movement of the first end piece with respect to the second end piece; and
   b) the at least one tissue activator is arranged at a distance from the one of the first end piece and the second end piece and extends perpendicular to the longitudinal axes L1 and L2;
   (iv) a first load bearing element directly coupled to the at least one tissue activator; and
   (v) a second load bearing element passing through the at least one tissue activator without contact with the at least one tissue activator.

2. The implant according to claim 1, wherein a first tissue activator (4a) is connected to the first end piece and a second tissue actuvator (4b) is connected to the second end piece, the implant further comprising a spring element arranged between the first tissue activator (4a) and the second tissue activator (4b).

3. The implant (1) according to claim 1 wherein the at least one tissue activator includes a first tissue activator and a second tissue activator arranged relative to one another to permit ingrowth of tissue, wherein the first load bearing element is directly coupled to the first tissue activator and the second load bearing element passes through the first tissue activator without contact with the first tissue activator.

4. The implant (1) according to claim 3, wherein each of the first tissue activator andthe second tissue activator is plate-like, bar-like, mesh-like or rod-shaped.

5. The implant (1) according to claim 3, wherein each of the first tissue activator and the second tissue activator is porous.

6. The implant (1) according to claim 1, wherein opposing surfaces of the at least one tissue activator are parallel, curved or oblique.

7. The implant (1) according to claim 1, wherein the at least one tissue activator includes a tissue-compatible plastic, a metal, a metal alloy or a ceramic material.

8. The implant (1) according to claim 1, wherein the at least one tissue activator includes a bioresorbable material.

9. The implant (1) according to claim 1, wherein at least one of a surface of the at least one tissue activator or an interstice between the at least one tissue activator and an adjacent tissue activator comprises a substance that promotes healing and bone building.

10. The implant (1) according to claim 1, wherein at least one of a surface of the at least one tissue activator or an interstice between the at least one tissue activator and an adjacent tissue activator comprises stem cells.

11. The implant (1) accordign to claim 1, wherein an interstice between the at least one tissue activator and an adjacent tissue activator has an open-pore structure.

12. The impland (1) according to claim 1, wherein each of the first end piece and the second end piece is configured to mechanically or chemically couple to the two bone fragments.

13. The implant (1) according to claim 1, wherein the at least one tissue activator comprises a first tissue activator (4a) and the implant further comprises a second tissue activator (4b), the first end piece (2) is connected by the first load-bearing element (7a) with the first tissue activator (4a), and the second end piece (3) is connected by the second load-bearing element (7b) with the second tissue activator (4b).

14. The implant (1) according to claim 1, wherein the implant is suitable for treatment of bone fractures and bone defects and for growing bone tissue.

15. A method for growing soft tissue or bone for therapeutic or aesthetic applications, the method comprising implanting an implant according to claim 1.

16. An implant (1) for modifying tissue deformation during bone healing between two bone fragments (5;6), the implant comprising:
   a first end piece (2) configured to be fastened to a first bone fragment (5) with a longitudinal axis L1;
   a first tissue activator (4a) arranged at a first distance from the first end piece, the first tissue activator extending perpendicular to the longitudinal axis L1;
   a first load bearing element (7a) directly coupling the first tissue activator to the first end piece;

a second end piece (3) configured to be fastened to a second bone fragment (6) with a longitudinal axis L2;

a second tissue activator (4b) arranged at a second distance from the second end piece, the second tissue activator extending perpendicular to the longitudinal axis L2;

a second load bearing element (7b) directly coupling the second tissue activator to the second end piece, the second load bearing element passing through the first tissue activator without contact with the first tissue activator, wherein the first end piece and the second end piece are loosely meshed with one another by the first tissue activator and the second tissue activator to allow relative movement of the first end piece with respect to the second end piece.

* * * * *